United States Patent [19]

Takami

[11] Patent Number: 4,963,960
[45] Date of Patent: Oct. 16, 1990

[54] ELECTRONIC ENDOSCOPE APPARATUS EMPLOYING AUTOMATIC LIGHT SOURCE CONTROL

[75] Inventor: Osamu Takami, Tochgi, Japan

[73] Assignee: Kabushiki Kaisha Toshiba, Kawasaki, Japan

[21] Appl. No.: 360,156

[22] Filed: Jun. 1, 1989

[30] Foreign Application Priority Data

Jun. 1, 1988 [JP] Japan ................................ 63-132822

[51] Int. Cl.$^5$ ................................................ A61B 1/06
[52] U.S. Cl. .......................................... 358/98; 128/6
[58] Field of Search .................... 358/98, 100, 93, 211; 128/4–6

[56] References Cited

U.S. PATENT DOCUMENTS

| | | | |
|---|---|---|---|
| 4,433,675 | 2/1984 | Konoshima | 128/6 |
| 4,561,429 | 12/1985 | Sato et al. | 128/6 |
| 4,646,724 | 3/1987 | Sato et al. | 358/98 X |

*Primary Examiner*—James J. Groody
*Assistant Examiner*—Victor R. Kostak
*Attorney, Agent, or Firm*—Foley & Lardner, Schwartz, Jeffery, Schwaab, Mack, Blumenthal & Evans

[57] ABSTRACT

In an electronic endoscope apparatus, a light source such as a xenon lamp is automatically turned off when the endoscope examination is accomplished, under the control of a video signal processing unit. The electronic endoscope apparatus includes a light source for illuminating an interior portion of a biological body under medical examination; an image sensor for imaging the interior portion of the biological body by receiving light reflected therefrom to produce an image signal; a converter for converting the image signal into a corresponding video signal; and, a signal processing unit for detecting that variations in levels of the video signal are continued for a predetermined duration time to output a detection signal, and for turning off the light source in response to the detection signal.

25 Claims, 4 Drawing Sheets

ELECTRONIC ENDOSCOPE APPARATUS EMPLOYING AUTOMATIC LIGHT SOURCE CONTROL

BACKGROUND OF THE INVENTION

1. Field of the Invention

The present invention generally relates to an electronic endoscope apparatus for displaying an interior image of a biological body under medical examination by utilizing an image scanner with a light source. More specifically, the present invention is directed to an electronic endoscope apparatus employing an automatic light source controller to automatically turn OFF a light source when an endoscope examination is completed, or interrupted for a predetermined duration time.

2. Description of the Related Art

A conventional electronic endoscope apparatus is arranged with the following construction to observe an interior portion of a biological body for a medical purpose.

A specific interior portion within the biological body is illuminated by illumination light. The light is emitted from a light source such as a xenon lamp mounted on the electronic endoscope apparatus, and transferred via a light guide, made of, for instance, an optical fiber, to a distal end of a scope.

A solid-state imaging element, e.g., a charge-coupled device (referred to as a "CCD"), similarly mounted on the distal end of the scope, receives light reflected from the specific illuminated interior portion, and thereafter converts the reflected light image of the specific interior portion into a corresponding image signal. The image signal is further converted by a camera control unit (referred to as a "CCU") into a video signal.

The video signal is then processed in a video signal processing circuit and/or a digital scan converter (referred to as a "DSC") for the image reconstruction process, and thereafter displayed on a CRT monitor.

All of the above-described functions are under control of a central processing unit (referred to as a "CPU").

In the conventional electronic endoscope apparatuses, to turn off the light source, an operator must manipulate a light source switch. In other words, the light source is manually controlled in the conventional electronic endoscope apparatus. As a result, a xenon lamp, or other types lamps forming of the light source remains turned-ON even after the endoscope diagnostic operation is completed.

In this case, since the lighting duration time of the xenon lamp or the like directly an influences the life thereof, there is a problem that the life time is furthermore shortened while the lamp is turned ON even after the endoscope diagnostic operation.

In addition, it is known that according to the brightness characteristics of a xenon lamp, the brightness is conspicuously lowered within a relatively short duration time since a new xenon lamp is turned ON.

Therefore, in case that a xenon lamp is employed in the light source of the electronic endoscope apparatus, unnecessary lighting time period must be reduced as shortly as possible.

On the other hand, the lamp power consumption is relatively large, as compared with the total power consumption of the electronic endoscope apparatus. Accordingly, unnecessary lighting of the lamp causes higher power cost of the electronic endoscope apparatus.

SUMMARY OF THE INVENTION

The present invention has been made in an attempt to solve the above-described conventional problems and, therefore has an object to provide an electronic endoscope apparatus capable of operating a light source at a higher efficiency, and also of prolonging the life of a lamp, comprising:

a light source (9) for illuminating an interior portion of a biological body under medical examination;

an image sensor (11) for imaging the illuminated interior portion of the biological body by receiving light reflected therefrom to produce an image signal;

a converter (12) for converting the image signal into a corresponding video signal; and, a signal processing unit (13:50) for detecting that variations in levels of the video signal are continued for a predetermined duration time to output a detection signal, and for turning off the light source (9) in response to the detection signal.

BRIEF DESCRIPTION OF THE DRAWINGS

Other characteristics and advantages of the present invention will appear more readily from a reading of the following description of particular embodiments in conjunction with the accompanying drawings, in which.

DETAILED DESCRIPTION OF THE PREFERRED EMBODIMENTS

Basic Idea

Before proceeding with various preferred embodiments, a basic idea of the present invention will now be described.

In an electronic endoscope apparatus where an interior portion of a biological body under medical examination is illuminated by illumination light projected from a light source such as a xenon lamp so as to produce a video signal, and an image of the illuminated interior portion is displayed in response to the video signal, variations in signal levels of a light-source controlling basis signal, e.g., either the video signal, or air feeding/cleaning-water feeding operation signals with respect to a lapse time are detected. That is, for instance, the variations in these signals when the endoscope examination is performed, and also is interrupted are detected.

Then, a judgment is made whether or not the signal level variations are below a predetermined reference level.

Another detection is made whether or not such a condition that the signal level variations are under this reference level is continued during a preselected duration time.

If such a low level condition is continued for a preselected duration time, the light source is automatically turned OFF regardless of any operation by the endoscope operator.

As previously described, the above-described objects of the present invention can be achieved by the electronic endoscope apparatus where the completion of the endoscope examination and/or the interruption thereof is judged by the endoscope apparatus per se (for instance, the video signal processing unit), and thus the xenon lamp of the light source is automatically turned OFF based upon this judgment result.

FIRST ELECTRONIC ENDOSCOPE APPARATUS

Figure 1:
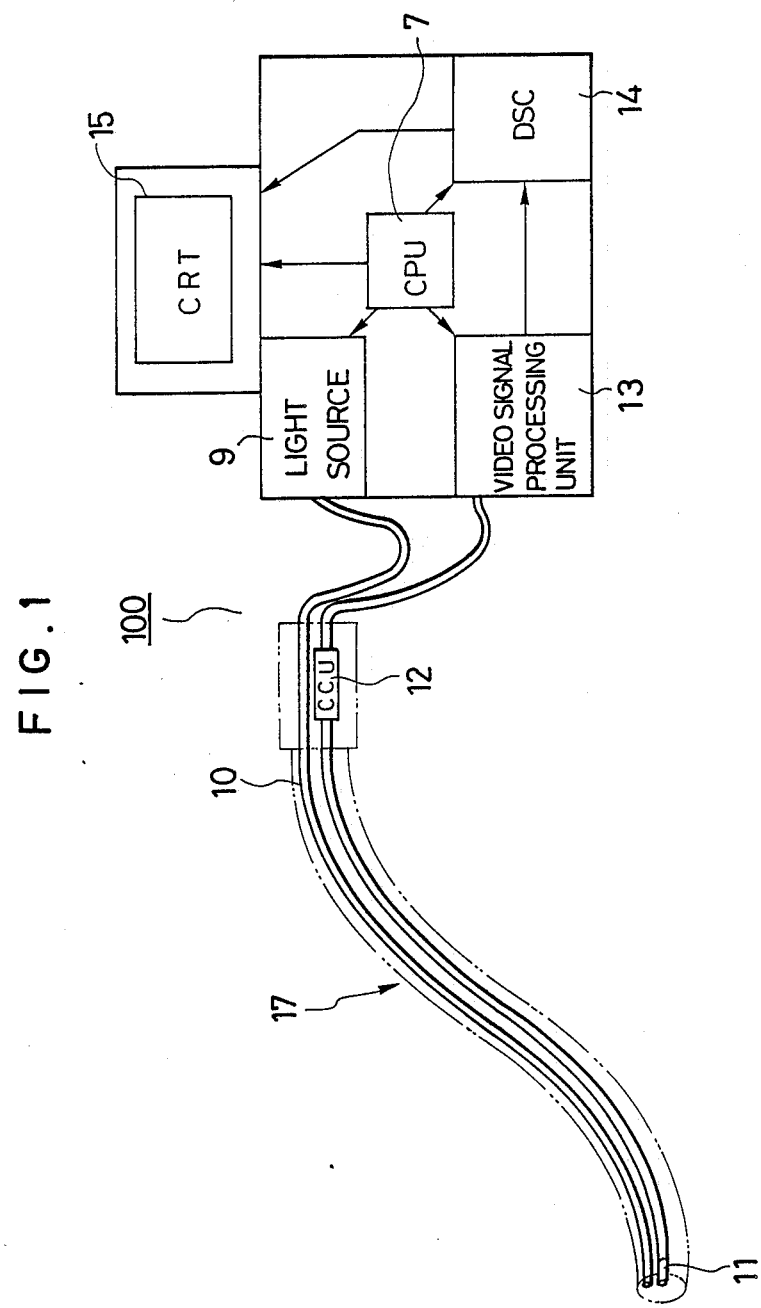
FIG. 1 schematically shows an electronic endoscope apparatus according to a first preferred embodiment of the invention.
Figure 2:
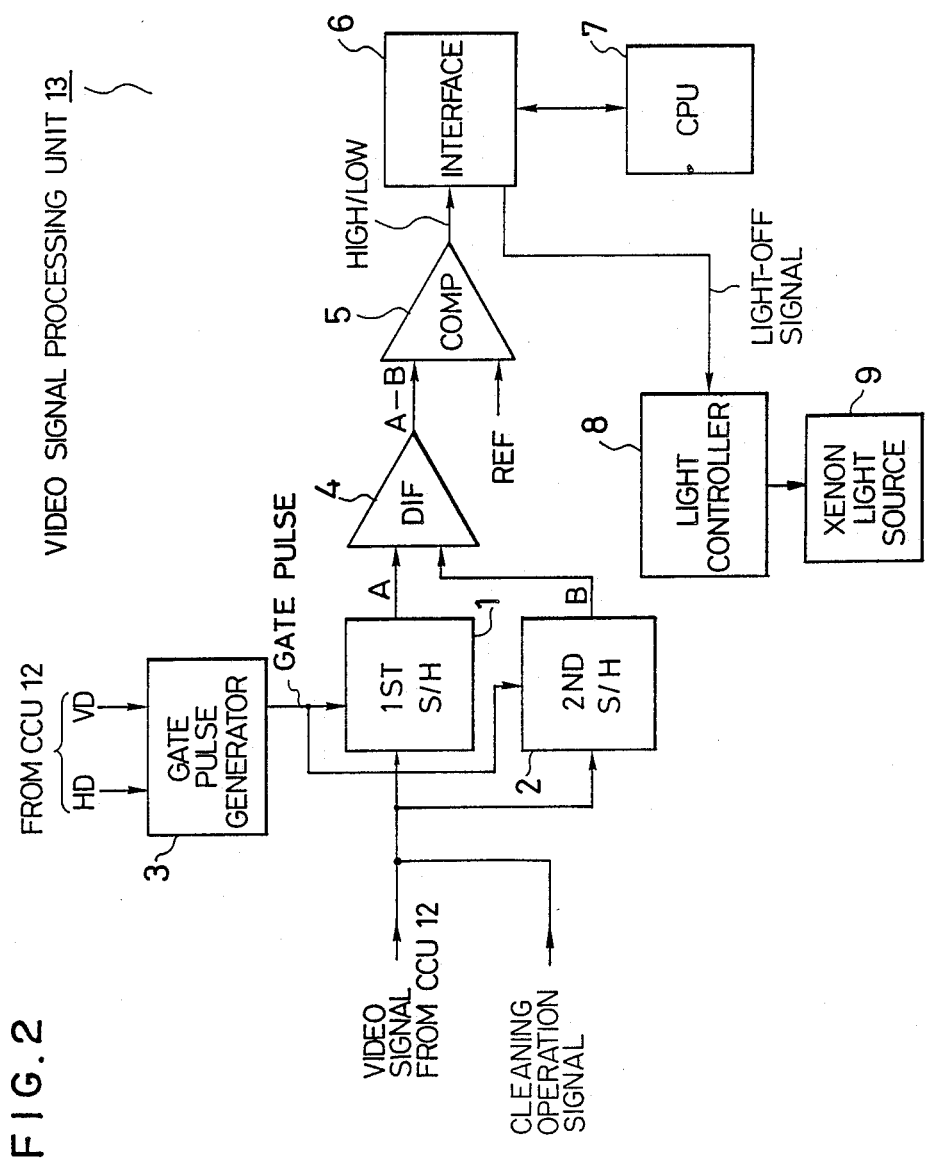
FIG. 2 is a block diagram of an video signal processing unit 13 employed in the endoscope apparatus shown in FIG. 1.
Figure 3:
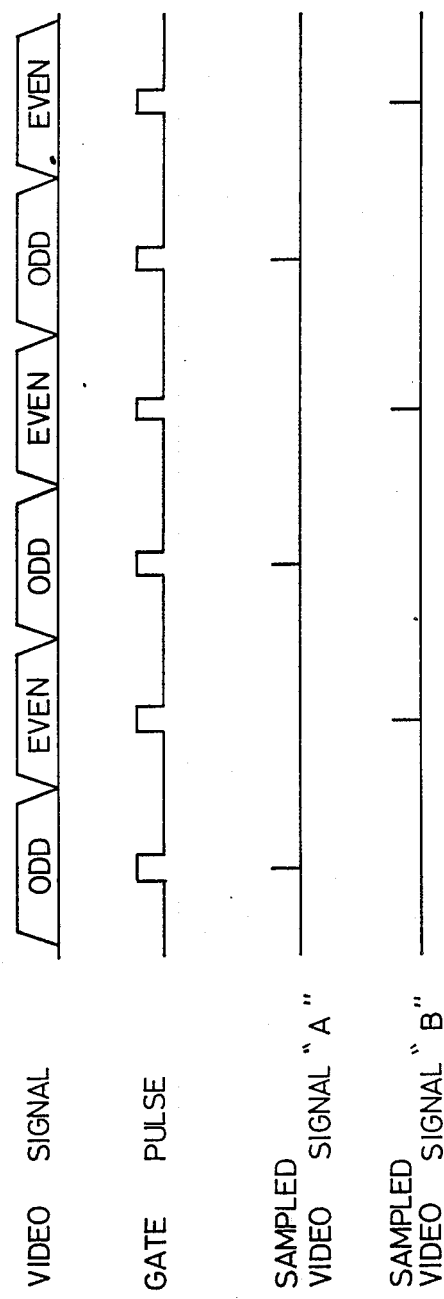
FIG. 3 is a waveform chart of the signals appearing in the video signal processing unit 13; and, FIG. 4 is a block diagram of an video signal processing unit 50 employed in an electronic endoscope apparatus according to a second preferred embodiment of the invention.

Referring now to FIGS. 1 to 3, an arrangement and a waveform chart of an electronic endoscope apparatus 100 according to a first preferred embodiment of the invention will be described.

FIG. 1 is a schematic block diagram of the endoscope apparatus 100, FIG. 2 is a schematic circuit diagram of the video signal processing unit 13 employed in the endoscope apparatus 100 shown in FIG. 1, and FIG. 3 is a waveform chart of signals in the video signal processing unit 13.

It should be noted that the first endoscope apparatus 100 controls the light source based upon variations in the acquired video signal levels.

In the electronic endoscope apparatus 100 according to the first preferred embodiment shown in FIG. 1, a CCD 11 receives light reflected from an interior portion of a biological body (not shown in detail) which is illuminated from a lamp, e.g., xenon lamp (not shown in detail) of a light source 9 via a light guide 10, and then converts the reflected light into a corresponding image signal. The image signal is processed in a CCU 12 to obtain a video signal. The video signal is inputted into a first sample/hold circuit 1 and also a second sample/hold circuit 2 (see FIG. 2).

A gate pulse generator 3 receives a horizontal synchronization (sync) signal "HD" and a vertical synchronization signal "VD" from CCU 12 so as to generate gate pulses. These gate pulses are supplied to the first and second sample/hold circuits 1 and 2 as a gate timing signal, respectively (see FIG. 3). In response to these corresponding gate pulses, the first and second sample/hold circuits 1 and 2 alternately sample the entered video signals at predetermined time intervals (see FIG. 3). Generally speaking, these time intervals are selected to be several milliseconds. Also, these sample/hold circuits 1 and 2 hold the input video signals until the subsequent sampling time. As apparent from FIG. 3, the first sample/hold circuit 1 samples the entered video signal at every odd field, whereas the second sample/hold circuit 2 samples the entered video signal of every even field.

The video signals "A" and "B" which have been sampled/held in these sample/hold circuits 1 and 2 are furnished to a differential amplifier 4 and thus differentially amplified therein so as to output a difference signal "A-B" as represented in FIG. 2. Then, the difference signal "A-B" is inputted to one input terminal of a comparator 5. A reference level signal is supplied to the other input terminal of the comparator 5.

The comparison results of this comparator 5 are as follows. That is, when the level of the difference signal exceeds the reference level, a "HIGH" level voltage is produced from the output terminal of the comparator 5. Conversely, when the level of the difference signal is lower than the reference level, a "LOW" level voltage is produced from the output terminal of the comparator 5.

The comparison result signal "HIGH" or "LOW" as the light-source controlling basis signal is inputted via an interface 6 to CPU 7. CPU 7 will judge that the comparison result signal has a "HIGH" or "LOW" level. It should be noted that this central processing unit 7 may be exclusively used only for the endoscope apparatus 100, or may be employed in the video signal processing unit 13.

Also, CPU 7 continuously judges the level of the comparison result signal for a predetermined duration time, i.e., one judging duration time. This judging duration time is normally selected to be several minutes. During this judging time period, only when CPU 7 continuously receives the comparison result signals having the LOW levels from the comparator 5 via the interface 6, a decision is made that the endoscope diagnostic operation is accomplished, or interrupted, so that CPU 7 produces a light-OFF signal.

These judging operations will now be summerized. The comparator 5 judges whether or not the difference signal is lower than the reference level. CPU 7 judges whether or not such a low-leveled condition is continued for a predetermined duration time.

The light-OFF signal is supplied to a light source 9 via the interface 6 and a light control circuit 8 so as to turn OFF the xenon lamp (not shown in detail).

On the other hand, when the comparison result signal having the HIGH level is entered into CPU 7 during one judging duration time, this judgment operation by CPU 7 is immediately completed, and thereafter CPU 7 commences its judgment in the next judging duration time. This operation may be realized by, for instance, resetting a counter (not shown in detail) of CPU 7.

SECOND ELECTRONIC ENDOSCOPE APPARATUS

Figure 4:
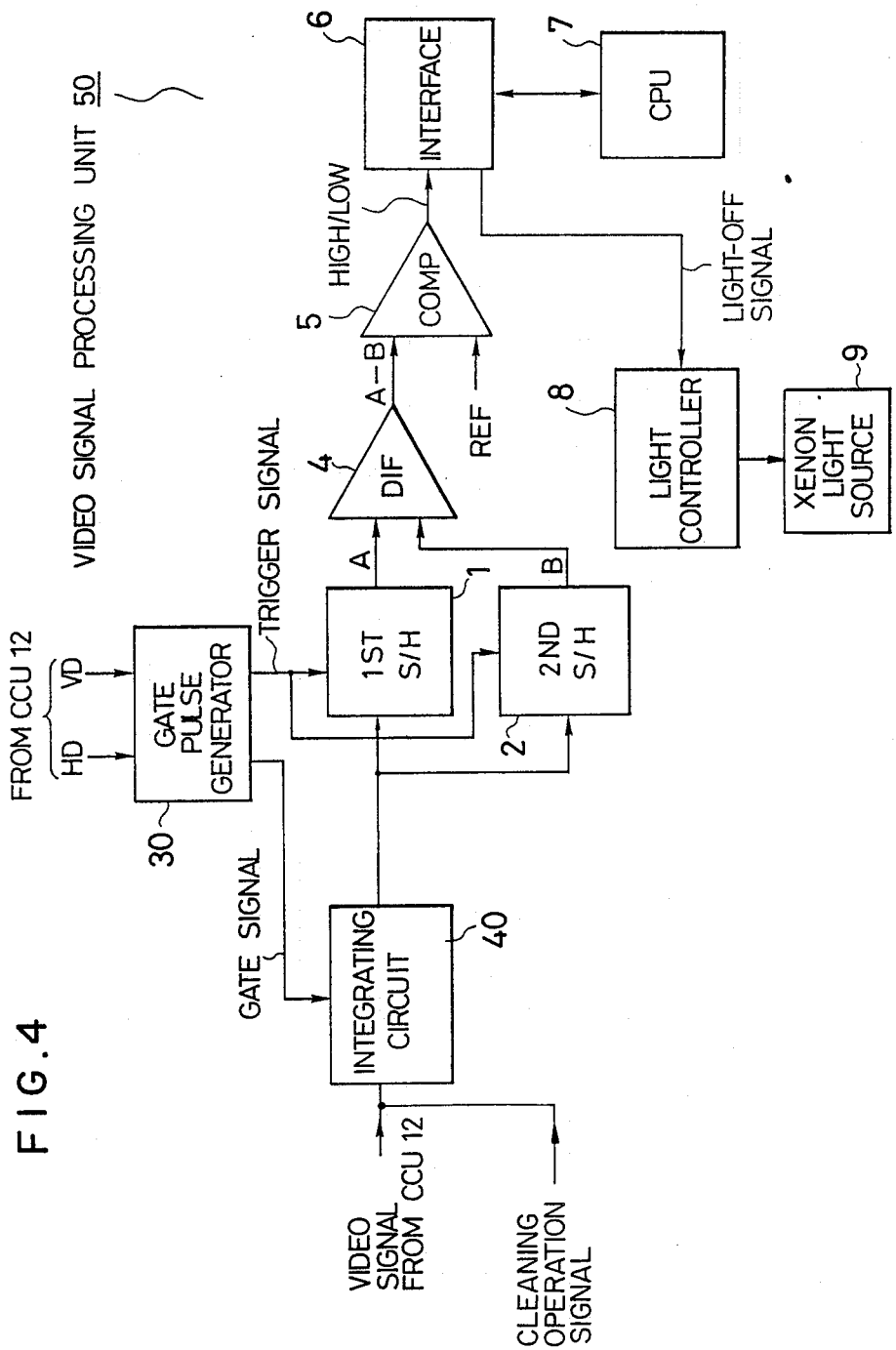

Referring now to a video signal processing circuit 50 shown in FIG. 4, an electronic endoscope apparatus according to second preferred embodiment of the invention will be described.

As apparent from the video signal processing circuit 50, since the major circuit thereof is the same as that of the video signal processing circuit 13, only different circuit operation will now be described.

The video signal derived from CCU 12 is supplied to an integrating circuit 40. In the integrating circuit 40, an integrating range for the input video signal is determined in response to a gate signal sent from a timing signal generator 30, and the input video signal is integrated. Thus, the integrated video signal is similarly sampled/held by the first and second sample/hold circuits 1 and 2 in response to trigger signals derived from the timing signal generator 30.

Features of the above-described second electronic endoscope apparatus are as follows in addition to the above-mentioned features of the first electronic endoscope apparatus. That is, there is a particular advantage that any adverse influence from noise contained in the video signal can be considerably reduced. When, for instance, an insect flies across a front surface of CCD 11 of the scope 17 which has been taken out from the interior portion of the biological body after the examination is completely, high-leveled signals are instantaneously contained in the video signal. However, according to the integrating operation of the circuit 40, since such an instantaneously high-leveled signal and also high-leveled signals which are continuously produced during a short duration time are integrated, the comparison result signal remains low and therefore the erroneous operations of the light control circuit 8 can be prevented.

MODIFICATIONS

The present invention is not restricted to the above-described preferred embodiments, but may be modified, or substituted by an ordinary skilled engineer without departing from the technical scope and spirit of the present invention.

In the above-described first and second preferred embodiment, the video signal derived from CCU 12 is used as the basis signal for controlling the light source 9 (i.e., light-source controlling basis signal). For instance, instead of this video signal, an air feeding/cleaning-water feeding operation signal may be utilized as this light-source controlling basis signal. That is to say, in general, water is fed to an object lens positioned in front of CCD and thereafter air is similarly fed thereto to dry the object lens for a cleaning purpose while the endoscope examination is carried out. As a consequence, if this cleaning operation is not executed for a predetermined time interval, it may be judged that the endoscope diagnostic operation is completed, or interrupted, so that the light source control can be performed according to the invention.

Also since the reference level and judgment duration time may be freely set, erroneous operation of the light source control may be properly avoided.

Although the above-described preferred embodiments checked the signal level variations in the light-source controlling basis signals, other basis signal may be utilized. For instance, a detector is employed to detect whether or not presence of an endoscope operating-condition detecting signal is continued for a predetermined time duration. Then, the lamp of the light source is turned off in response to the resultant signal of this detector. The endoscope operating-condition detecting signal is produced while the endoscope is under operation.

Moreover, instead of the scope means employing the CCD image sensor, a normal fiber scope may be utilized in the endoscope apparatus according to the invention.

While has been described above, according to the electronic endoscope apparatus of the invention, the completion or interruption of the endoscope diagnostic examination can be judged by the endoscope apparatus per se so as to automatically turn OFF the light source, whereby the lamp of the light source can be automatically turned OFF when the examination is completed or interrupted for a predetermined duration time. As a consequence, the life of an endoscope lamp can be prolonged and also the brightness characteristics of the xenon lamp can be improved. In addition, total power consumption of the electronic endoscope apparatus can be lowered.

What is claimed is:

1. An electronic endoscope apparatus comprising:
    a light source for illuminating an interior portion of a biological body under medical examination;
    an image sensor means for imaging the illuminated interior portion of the biological body by receiving light reflected therefrom to produce an image signal;
    means for converting the image signal into a corresponding video signal; and,
    signal processing means for detecting that variations in levels of a light-source controlling basis signal are continued for a predetermined duration time to output a detection signal representing the difference between the video signal and the basis signal, and for turning off the light source in response to the detection signal, said light-source controlling basis signal being produced in accordance with operation of the endoscope apparatus.

2. An electronic endoscope apparatus as claimed in claim 1, wherein said light-source controlling basis signal is derived from at least one of the video signal and a cleaning operation signal for the image sensor means which is produced while an object lens of the image sensor means is cleaned by feeding water and air thereto.

3. An electronic endoscope apparatus as claimed in claim 1, wherein said signal processing means is a video signal processing unit including:
    a gate pulse generator for generating a first gate pulse in response to a horizontal synchronization signal and a vertical synchronization signal;
    first and second sample/hold circuits for alternately sampling/holding the video signal at different timing periods in response to the gate pulse to output first and second sampled video signals;
    a differential amplifier for differentially amplifying the first and second sampled video signals to obtain a difference video signal;
    a comparator for comparing the difference video signal with a reference signal to output a comparison result signal; and,
    a central processing unit for processing the comparison result signal to firstly detect whether or not variations in the comparison result signals are below a predetermined low level, and to secondly detect whether or not the low-leveled variations are continued for a predetermined duration time.

4. An electronic endoscope apparatus as claimed in claim 3, wherein said first sample/hold circuit is for sampling/holding the video signal every odd fields of the video signal, whereas said second sample/hold circuit is for sampling/holding the video signal every even fields thereof.

5. An electronic endoscope apparatus as claimed in claim 3, wherein said detecting duration time of said central processing unit is selected to be at least several minutes.

6. An electronic endoscope apparatus as claimed in claim 1, wherein said signal processing means is a video signal processing unit including:
    a timing signal generator for generating a second gate pulse and a trigger signal in response to a horizontal synchronization signal and a vertical synchronization signal;
    an integrating circuit for integrating the video signal derived from the image signal converting means to output an integrated video signal;
    first and second sample/hold circuits for alternately sampling/holding the integrated video signal at difference timing periods in response to the trigger signal to output first and second sampled video signals;

a differential amplifier for differentially amplifying the first and second sampled video signals to obtain a difference video signal;

a comparator for comparing the difference video signal with a reference signal to output a comparison result signal; and, a central processing unit for processing the comparison result signal to firstly detect whether or not variations in the comparison result signals are below a predetermined low level, and to secondly detect whether or not the low-leveled variations are continued for a predetermined duration time.

7. An electronic endoscope apparatus as claimed in claim 6, wherein said first sample/hold circuit is for sampling/holding the video signal every odd field of the video signal, whereas said second sample/hold circuit is for sampling/holding the video signal every even field thereof.

8. An electronic endoscope apparatus as claimed in claim 6, wherein said detecting duration time of said central processing unit is selected to be at least several minutes.

9. An electronic endoscope apparatus as claimed in claim 1, wherein said light source is an xenon lamp.

10. An endoscope apparatus comprising:
a light source for illuminating an interior portion of a biological body under medical examination;
detecting means for detecting operations of the endoscope apparatus to output an endoscope operating-condition detecting signal;
signal processing means for detecting that presence of the endoscope operating-condition detecting signal is continued for a predetermined duration time to output a light-source controlling signal; and,
light source controlling means for turning off the light source in response to the light-source controlling signal.

11. An endoscope apparatus as claimed in claim 10, wherein said light-source controlling signal is derived from a cleaning operation signal for an object lens cleaned by feeding water and air thereto.

12. An endoscope apparatus as claimed in claim 10, wherein said detecting duration time of said signal processing means is selected to be at least several minutes.

13. An endoscope apparatus as claimed in claim 10, wherein said light source is an xenon lamp.

14. An electronic endoscope apparatus comprising:
a light source for illuminating an interior portion of a biological body under medical examination;
an image sensor means for imaging the illuminated interior portion of the biological body by receiving light reflected therefrom to produce an image signal;
means for converting the image signal into a corresponding video signal; and,
signal processing means for detecting that variations in levels of said video signal are continued for a predetermined duration time to output a detection signal, and for turning off the light source in response to the detection signal, said level variations in the video signal being caused by operation of the endoscope apparatus.

15. An electronic endoscope apparatus as claimed in claim 14, wherein said signal processing means is a video signal processing unit including:
a gate pulse generator for generating a gate pulse in response to horizontal synchronization signals and vertical synchronization signals;
first and second sample/hold circuits for alternately sampling/holding video signals at different timing periods in response to gate pulses to output first and second sampled video signals;
a differential amplifier for differentially amplifying the first and second sampled video signals to obtain a difference video signal;
a comparator for comparing the difference video signal with a reference signal to output a comparison result signal; and,
a central processing unit for processing the comparison result signal to firstly detect whether or not variations in the comparison result signals are below a predetermined level, and secondly to detect whether of not such low level variations are continued for a predetermined duration.

16. An electronic endoscope apparatus as claimed in claim 15, wherein said first sample/hold circuit is for sampling/holding the video signal every odd field of the video signal, whereas said second sample/hold circuit is for sampling/holding the video signal every even field thereof.

17. An electronic endoscope apparatus as claimed in claim 15, wherein said detecting duration time of said central processing unit is selected to be less than 10 minutes.

18. An electronic endoscope apparatus as claimed in claim 14, wherein said signal processing means is a video signal processing unit including:
a timing signal generator for generating second gate pulses and trigger signals in response to a horizontal synchronization signal and a vertical synchronization signal;
an integrating circuit for integrating the video signal derived from the video signal converting means to output an integrated video signal;
first and second sample/hold circuits for alternately sampling/holding the integrated video signal at different timing periods in response to the trigger signal, to output first and second sampled video signals;
a differential amplifier for differentially amplifying the first and second sampled video signals to obtain a difference video signal;
a comparator for comparing the difference video signal with a reference signal to output a comparison result signal; and,
a central processing unit for processing the comparison result signal to firstly detect whether or not variations in the comparison result signals are below a predetermined level, and secondly to detect whether or not the low level variations are continued for a predetermined duration.

19. An electronic endoscope apparatus as claimed in claim 18, wherein said first sample/hold circuit is for sampling/holding the video signal every odd field of the video signal, whereas said second sample/hold circuit is for sampling/holding the video signal every even field thereof.

20. An electronic endoscope apparatus as claimed in claim 18, wherein said detecting duration time of said central processing unit is selected to be less than 10 minutes.

21. An electronic endoscope apparatus as claimed in claim 14, wherein said light source is an xenon lamp.

22. An electronic endoscope apparatus comprising:
a light source for illuminating an interior portion of a biological body under medical examination;

an image sensor means for imaging the illuminated interior portion of the biological body by receiving light reflected therefrom to produce an image signal;

detecting means for detecting a cleaning operation for the image sensor means to output a cleaning operation detecting signal;

signal processing means for detecting that the cleaning operation detecting signal continues for a predetermined duration time to output a light source controlling signal; and, light source controlling means for turning off the light source in response to the light source controlling signal.

23. An endoscope apparatus as claimed in claim 22, wherein said light source controlling signal is produced while an object lens of the image means is cleaned by feeding water and air thereto.

24. An endoscope apparatus as claimed in claim 22, wherein said detecting duration time of said signal processing means is selected to be less than 10 minutes.

25. An endoscope apparatus as claimed in claim 22, wherein said light source is an xenon lamp.

* * * * *